(12) United States Patent
Chen et al.

(10) Patent No.: US 8,585,719 B2
(45) Date of Patent: Nov. 19, 2013

(54) INSTRUMENT FOR ANORECTAL SURGERY

(75) Inventors: Wangdong Chen, Jiangsu (CN);
Shuicheng Ding, Jiangsu (CN); Jing Zhou, Jiangsu (CN)

(73) Assignee: Suzhou Touchstone International Medical Science Co., Ltd., Jiangsu (CN)

( * ) Notice: Subject to any disclaimer, the term of this patent is extended or adjusted under 35 U.S.C. 154(b) by 223 days.

(21) Appl. No.: 12/810,693

(22) PCT Filed: Dec. 25, 2008

(86) PCT No.: PCT/CN2008/002068
§ 371 (c)(1),
(2), (4) Date: Jun. 25, 2010

(87) PCT Pub. No.: WO2009/092194
PCT Pub. Date: Jul. 30, 2009

(65) Prior Publication Data
US 2010/0280523 A1    Nov. 4, 2010

(30) Foreign Application Priority Data

| Dec. 27, 2007 | (CN) | 2007 2 0129937 U |
| Jan. 14, 2008 | (CN) | 2008 2 0030849 U |
| Sep. 11, 2008 | (CN) | 2008 2 0185869 U |
| Sep. 11, 2008 | (CN) | 2008 2 0185870 U |
| Nov. 4, 2008 | (CN) | 2008 1 0174395 |
| Nov. 26, 2008 | (CN) | 2008 2 0217049 U |
| Nov. 27, 2008 | (CN) | 2008 2 0217182 U |
| Dec. 1, 2008 | (CN) | 2008 2 0217314 U |

(51) Int. Cl.
*A61B 17/04* (2006.01)

(52) U.S. Cl.
USPC ............ 606/148; 606/197; 600/184

(58) Field of Classification Search
USPC .......... 606/148, 190, 191, 197; 600/184, 185, 600/186, 201
See application file for complete search history.

(56) References Cited

U.S. PATENT DOCUMENTS

| 6,083,241 A | 7/2000 | Longo et al. ................. 606/219 |
| 2008/0275306 A1* | 11/2008 | Rebuffat et al. .............. 600/184 |

FOREIGN PATENT DOCUMENTS

| CN | 2009/42077 | 9/2007 | ............... A61B 1/31 |
| WO | 2007/016946 | 2/2007 | ............... A61B 1/32 |
| WO | 2007/049308 | 5/2007 | ............... A61B 1/31 |

OTHER PUBLICATIONS

Merriam-Webster definition for "integrate" as viewed on Nov. 8, 2012; http://www.merriam-webster.com/dictionary/integrate.*

*Primary Examiner* — Ryan Severson
*Assistant Examiner* — Jonathan W Miles
(74) *Attorney, Agent, or Firm* — Allen, Dyer, Doppelt, Milbrath & Gilchrist, P.A.

(57) ABSTRACT

The present invention provides an instrument for anorectal surgery, comprising a hollow main body, a suture junction disposed at a rear end of the main body and an inserting guider disposed at a front end of the main body. At an operating position, all or part of mucosa and tissues can get through the main body. At least one opening is made in the wall of the main body, and all or part of the mucosa and tissues can get into a hollow interior of the main body through the opening. Because of the openings on the wall of the main body, the present invention can be operated to perform the anorectal surgery of local and non-annular cutting, which facilitates a quick surgical operation, further allays the pain of the patients, and a better operation effect is obtained.

8 Claims, 8 Drawing Sheets

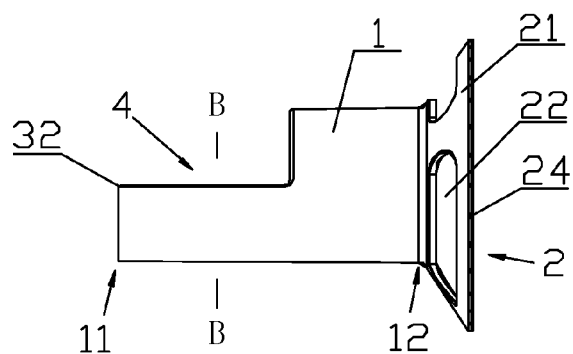
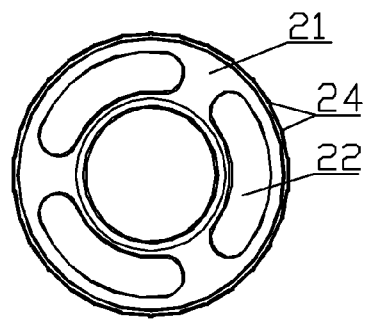
Fig.9
Fig.10
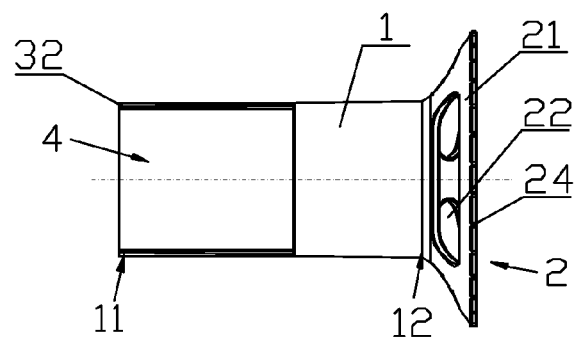
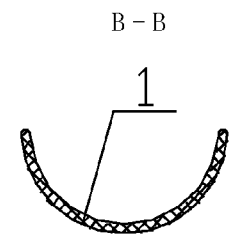
Fig.11
Fig.12

INSTRUMENT FOR ANORECTAL SURGERY

TECHNICAL FIELD

The present invention relates to an instrument for anorectal surgery, more particularly, to a new instrument for operations of cutting hemorrhoids, rectal polyp, rectocele and so on in the technical field of medical instrument.

BACKGROUND OF THE INVENTION

The diseases of Anorectum Section mainly refer to the diseases of anus, rectum and colon. Common anorectal diseases include internal hemorrhoids, external hemorrhoids, anal fissure, anal fistula, proctoptoma, rectal polyp, rectocele and so on. The colopathy includes ulcerative colitis, colonic polyps, colonic diverticulitis, colonic tumor and so on.

There is a method called PPH in the surgery operation of removal of hemorrhoids, namely, the Procedure for Prolapse and Hemorrhoids with the conventional circular stapler. The principle of PPH are as follows: the internal hemorrhoids, the mucosa and submucosa on the hemorrhoids are cut for about 3 cm-4 cm on condition that the anal tissues are conserved; the two ends are anastomosed, while the blood supply to hemorrhoids is blocked, to pull up and fix the deciduous tissues, so that the anal canal and rectum in pathology state are restored to normal anatomic state. Operative treatment for the severe hemorrhoids with PPH has advantages of allaying the pain and reducing bleeding amount after the operation, shortening hospital stay, speeding up recovery period, no influence on daily life, low recurrence rate, etc. However, in clinical practice, some patients do not have three but one or two abnormal hemorrhoids simultaneously. If the conventional circular stapler is used to cut around, three hemorrhoids will all be cut no matter whether they are in normal or abnormal states. The operation will harm the patients and has no positive influences on rehabilitation after the operation. Furthermore, for the reason that the conventional circular stapler is a circumferential device for cutting and suturing, after the conventional circular stapler cuts and sutures all or part of the mucosa and tissue coordinating with the conventional anal speculum pedestal, there will be suture and incision around the rectum, and also a lap of pins at the suture and incision, which makes the suture and incision become abnormally rigid and inflexible. When the patients are defecating, the suture and incision may be distracted and need to be sutured again, which will increase the pain of the patients and increase the medical expenditures.

On the other hand, the rectal polyp in the anorectal diseases generally refers to the protrusion lesion of the rectal mucosa surface extruding to the rectum cavity, and includes adenoma, children polyp, inflammatory polyp and polyposis. It is known in recent years that the polyp is a kind of lesion inducing colorectal cancers, and cutting the polyp as soon as possible can prevent the cancers from occurring. So the polyp as the precancerous lesion has attracted more attention. The rectocele, or protuberance of the rectal anterior wall, also known as proctocele, is one of the syndromes of the exit obstruction. The rectal wall of the patient extrudes into the vagina due to the thin rectovaginal septum, just like a hernia. At present, there are mainly three methods as follows for treating the two kinds of diseases described above:

1. Surgical repairer via rectum. There are two particular methods as follows:
   I. At the bottom of the rectum and 0.5 cm above the tooth trace, make a longitudinal incision about 7 cm long and deep into the submucosal to make the muscle exposed. Dissociate the mucosal flap on both sides for 1 cm to 2 cm according to the width of the rectocele. Then suture with chromic catgut of model 2/0, and close the left edge of the musculi levator ani. At last, repair the flap on both sides and make intervening suture for the mucosal incision with chromic catgut.
   II. Make a transverse incision about 1.5-2 cm long. Make longitudinal incisions about 7 cm long at two ends of the transverse incision respectively to form a U-shaped incision. Firstly, make intervening transverse suture for about 3 stitches to 4 stitches and suture the slack rectovaginal septum transversely. Secondly, make intervening longitudinal suture for about 2 stitches to 3 stitches, and cut the excess mucous membrane, and suture the edges of the mucosal muscle flap with the tooth line discontinuously. At last, suture the longitudinal incisions at the two ends of the transverse incision continuously or discontinuously.

2. Closed repair via rectum. The procedures of this method are as follows: clamp the muscularis mucosae longitudinally with curved forceps according to the size of the rectocele; then suture the muscularis mucosae from bottom to top continuously till to the symphysis pubis with the chromic catgut of model 2/0.

3. Closed suture for repairing the rectocele via rectum. The procedures of this method are as follows: make double breasted and continuous interlocking suture on the rectocele to suture the mucosa, the submucosa and the mucosal muscle together; eliminate sacs on the rectal anterior wall; tighten the continuous interlocking suture to make a strangulation and make the mucosa necrotic and deciduous, so that the wounds near the submucosa and the mucosal muscle heal quickly.

The disadvantages of the methods above are that, the procedures of the operations are too complicated, the suture is made by hand, the suturing speed is slow and the effects are not satisfactory.

SUMMARY OF THE INVENTION

The present invention is aimed at solving the problems of prior art by providing a new and multifunctional instrument for anorectal surgery, more particularly for operations of cutting hemorrhoids, rectal polyp, rectocele and so on.

The object of the present invention is achieved by the following technical scheme:

An instrument for anorectal surgery, comprising a hollow main body, the main body includes a front end and a rear end, wherein the rear end of the main body has a closed-ring cut section, and the main body can reach an operating position through an anus; at least one opening is made in a front wall of the closed-ring cut section of the main body; and tissues need to be cut can get into a hollow interior of the main body through the opening.

Preferably, a suture junction is disposed at the rear end of the main body; the main body can be pushed to the operating position by operating the suture junction and can be fixed at the operating position by suturing the suture junction on the tissues.

Preferably, the suture junction is a broad brim having a diameter greater than that of the main body, and the broad brim is backwardly divergent in shape. The broad brim has hollowed-out structures thereon, at least two hollowed-out structures are disposed evenly on the broad brim; two handles are disposed symmetrically and peripherally on the broad brim, alternatively, wavy projections are disposed at a circumference of the broad brim.

Alternatively, the suture junction is made as holes on the rear end of the main body.

Preferably, an inserting guider is disposed at the front end of the main body; and the instrument for anorectal surgery is guided to the operating position by the inserting guider.

Preferably, the inserting guider is a cone-shaped body, or is a chamfer on the front end of the main body.

Preferably, the main body is cylindrical or conical. The main body is formed fixedly by a front part and a rear part. The length of the opening is in the range of one sixth to five sixths of length of the main body.

Preferably, one opening is made in a wall of the main body and the opening has a central angle ranging from 80 degrees to 300 degrees; alternatively, two openings are made in a wall of the main body and each opening has a central angle ranging from 30 degrees to 160 degrees; alternatively, three openings are made evenly in a wall of the main body, and central angles of the three openings are all equal, or all different, or two of the central angles are equal.

Preferably, a scale is disposed in a wall of the main body to display how deep the main body enters the anus, and the scale covers part or all of the main body.

Preferably, on the front end of the main body are disposed a curved wall and an opening opposite to the curved wall; and tissues need to be cut can get into the hollow interior of the main body through the opening.

Preferably, the length of the curved wall is from 10 mm to 70 mm and the width is from 10 mm to 70 mm; the foremost-end of the curved wall is curved.

Distinguished from a surgical operation with the conventional anoscope, during the surgical operation with the instrument of the present invention, it is not necessary to use a cannula and an anoscope, and the corresponding processes for operating the two instruments are omitted, which makes the whole operation simpler and reduces the operation time. Because of the openings on the wall of the main body of the instrument, the present invention is better for performing the surgery operations of cutting single hemorrhoid or double hemorrhoids, which facilitates a quick surgical operation and further allays the pain of the patients. Moreover, coordinated with the circular stapler, the present invention can be applied in the anorectal surgery of non-circular cutting for single hemorrhoid, double hemorrhoids or rectocele, which improves the overall effect of the operation, and it is worth to promote the present invention in this field.

BRIEF DESCRIPTION OF THE DRAWINGS

The present invention will be described in more details with reference to the accompanying drawings:

FIG. 9 is a front view of the instrument for anorectal surgery according to the fourth embodiment of the present invention;

FIG. 10 is a right view of the fourth embodiment of the present invention;

FIG. 11 is a top view of the fourth embodiment of the present invention;

FIG. 12 is a sectional view cut along B-B line in FIG. 9;

| 1 main body | 11 front end | 12 rear end |
|---|---|---|
| 13 front part | 14 rear part | 2 suture junction |
| 21 broad brim | 22 hollowed-out structure | 23 handle |
| 24 projection | 25 holes | 3 inserting guider |
| 31 cone-shaped body | 32 chamfer | 4 opening |
| 5 scale | 6 curved wall | 7 closed-ring cut section |
| L length | D width | α central angle |

DETAILED DESCRIPTION OF THE PREFERRED EMBODIMENTS

The present invention provides an instrument for anorectal surgery.

Figure 1:
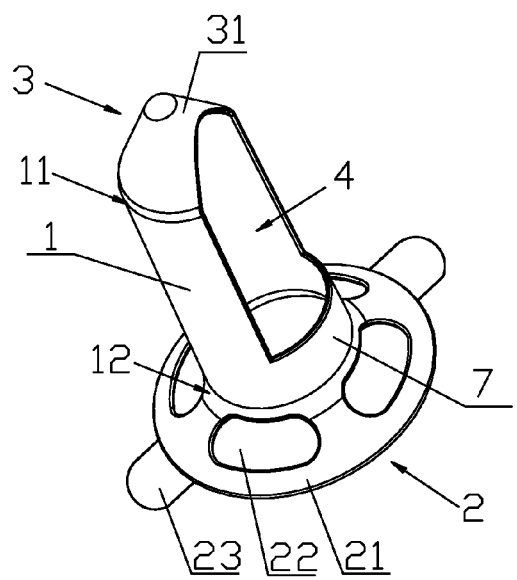
FIG. 1 is a schematic view illustrating the instrument for anorectal surgery according to the first embodiment of the present invention.

According to the embodiment shown in FIG. 1, the instrument mainly for hemorrhoid surgery of anorectal surgical operations comprises a hollow main body 1. The main body 1 comprises a front end 11 and a rear end 12. The rear end 12 of the present invention has a closed-ring cut section 7, more specifically is a cylindrical body, which is disposed to prevent normal tissues from falling into the hollow interior of the main body 1. At least one opening 4 is made in the front wall of the closed-ring cut section 7 of the main body 1. All or part of the mucosa and tissues can get into the hollow interior of the main body 1 through the opening 4. In all embodiments of the present invention, the instrument comprises a suture junction 2 disposed at the rear end 12 of the main body 1 and an inserting guider 3 disposed at the front end 11 of the main body 1.

In this preferred embodiment as shown in FIG. 1, the main body 1 is fixed at the operating position by suturing the suture junction 2 with the tissues, and the instrument for anorectal surgery is guided to the operating position by the inserting guider 3. If there is no need to fix the main body 1 with the tissues during the operation, the operator can push the main body 1 into the anus by simply operating the suture junction 2 and then hold it by hand.

At the operating position, all or part of the mucosa and tissues can get into the hollow interior of the main body 1 through the opening 4 and can go through the main body 1. The so called operating position refers to the location where the instrument for anorectal surgery is inserted into the patient's body, then all or part of the mucosa and tissues are pulled into the interior of the main body 1, and then all or part of the mucosa and tissues are cut with a suture instrument, and the incised tissues are sutured.

In this preferred embodiment, the main body 1 is cylindrical. Alternatively, the main body 1 can be conical so that it can be pushed into the patient's body more easily. The suture junction 2 is a broad brim 21 having a diameter greater than that of the main body 1, the broad brim 21 has hollowed-out structures 22 thereon and is backwardly divergent in shape. In this preferred embodiment, four hollowed-out structures 22 are distributed evenly on the surface of the broad brim 21. While only two or three hollowed-out structures 22 are needed to be distributed evenly on the surface of the broad brim in order to fix the instrument at the operating position steadily. Two handles 23 are disposed symmetrically and peripherally on the broad brim 21 in order that the doctor can hold the instrument with the handles. In this preferred embodiment, the inserting guider 3 is a cone-shaped body 31 which makes the main body 1 get into the patient's body more easily. The length of the opening 4 on the main body 1 is five sixths of the length of the main body 1. Of course, the length of the opening 4 can be set, normally in the range of one sixth to five sixths of the length of the main body 1, according to the need of different operations. In this preferred embodiment, in order to get a long opening 4 and for the convenience of producing, the opening 4 extends to cut a small part of the cone-shaped body 31. The central angle of the opening is from 80 degrees to 300 degrees, preferably 120 degrees.

Preferably, the main body 1 and the suture junction 2 of the instrument are made transparent for the convenience of the doctor's observing. And the cone-shaped body 31 is made opaque so that the visual field will not be affected by other tissues during the surgical operation.

Figure 2:
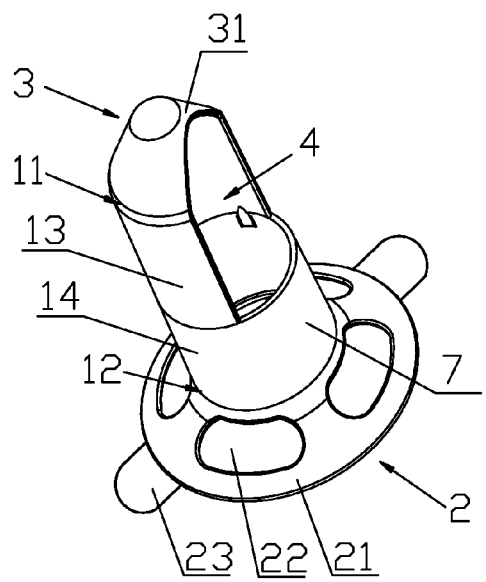
FIG. 2 is a schematic view illustrating the instrument for anorectal surgery according to the second embodiment of the present invention.
Figure 3:
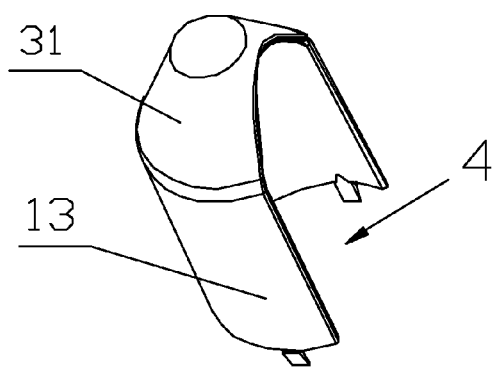
FIG. 3 is a schematic view illustrating the front part of the second embodiment of the present invention.
Figure 4:
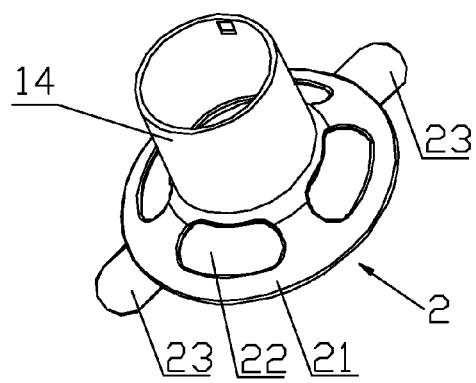
FIG. 4 is a schematic view illustrating the rear part of the second embodiment of the present invention.
Figure 5:
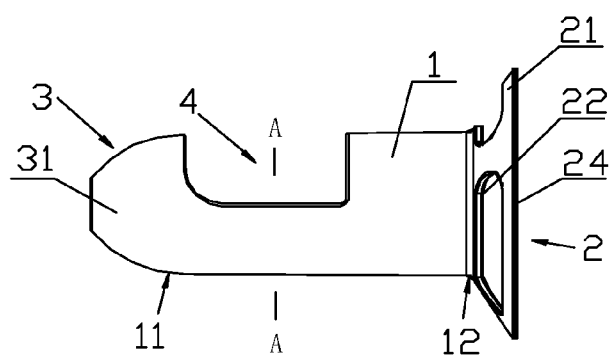
FIG. 5 is a front view of the instrument for anorectal surgery according to the third embodiment of the present invention.
Figure 6:
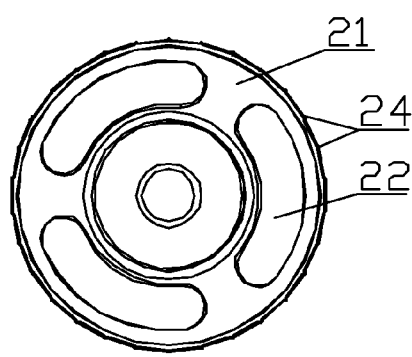
FIG. 6 is a right view of the third embodiment of the present invention.
Figure 7:
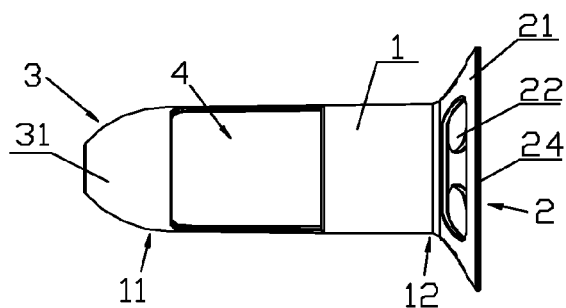
FIG. 7 is a top view of the third embodiment of the present invention.
Figure 8:
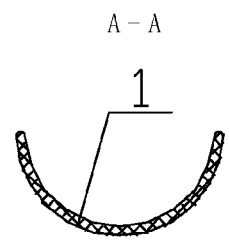
FIG. 8 is a sectional view cut along A-A line in FIG. 5.
Figure 13:
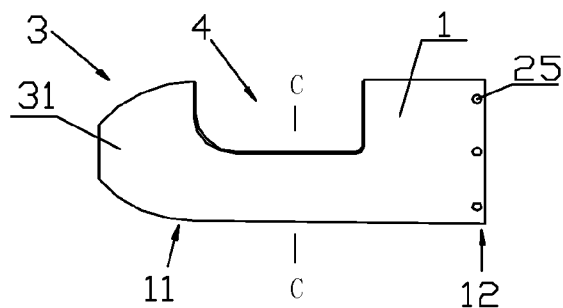
FIG. 13 is a front view of the instrument for anorectal surgery according to the fifth embodiment of the present invention.
Figure 14:
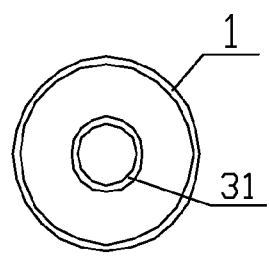
FIG. 14 is a right view of the fifth embodiment of the present invention.
Figure 15:
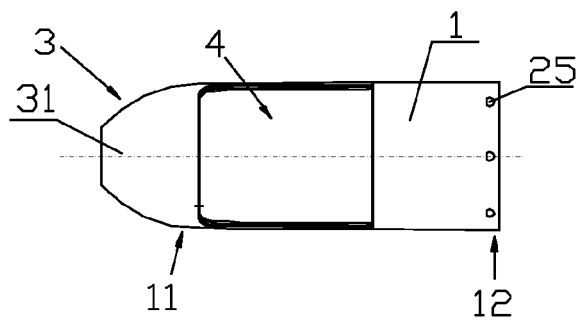
FIG. 15 is a top view of the fifth embodiment of the present invention.
Figure 16:
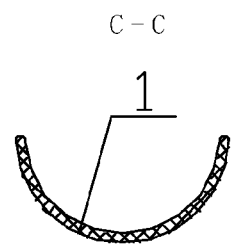
FIG. 16 is a sectional view cut along C-C line in FIG. 13.
Figure 17:
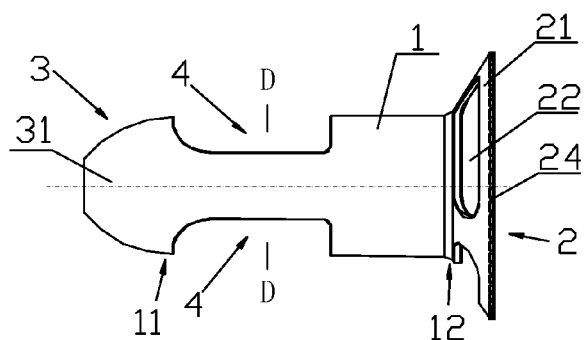
FIG. 17 is a front view of the instrument for anorectal surgery according to the sixth embodiment of the present invention.
Figure 18:
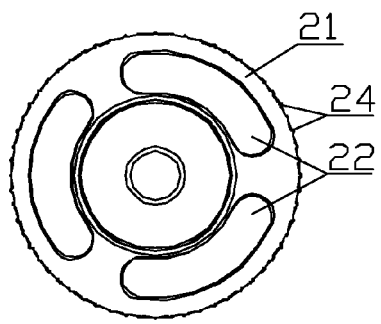
FIG. 18 a right view of the sixth embodiment of the present invention.
Figure 19:
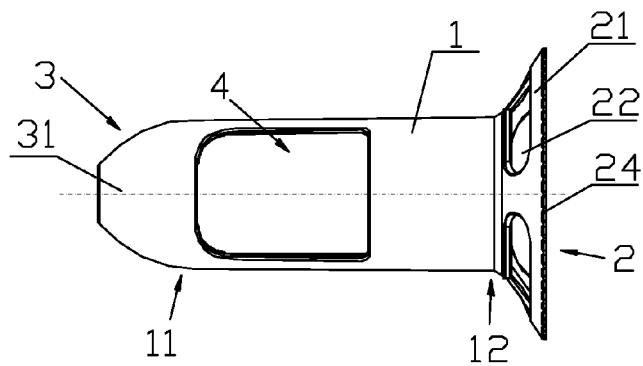
FIG. 19 is a top view of the sixth embodiment of the present invention.
Figure 20:
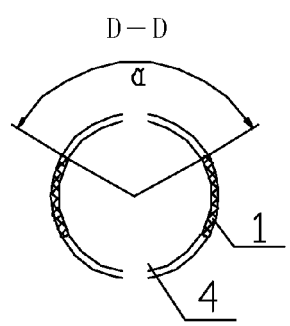
FIG. 20 is a sectional view cut along D-D line in FIG. 17.

The second embodiment of the present invention is illustrated in FIGS. 2-4. The second embodiment differs from the first embodiment in that the main body 1 is formed fixedly by a front part 13 and a rear part 14, wherein the front part 13 is integrated with the inserting guider 3 and the rear part 14 is integrated with the suture junction 2, for the convenience of assembling and replacing the instrument. That is, as shown in FIG. 3, the front part 13 is integrated with the cone-shaped body 31, and as shown in FIG. 4, the rear part 14 is integrated with the broad brim 21. In this embodiment, the front part 13 and the rear part 14 of the body are snap-fit connected, however, other connections, such as threaded connections, are not excluded from this invention. The opening 4 is disposed in the front part 13 of the main body 1 and the length of the opening 4 is one half of that of the main body 1. Same as in the first embodiment, in the second embodiment, the suture junction 2 is a broad brim 21 having a diameter greater than that of the main body 1, the broad brim 21 has hollowed-out structures 22 thereon and is backwardly divergent in shape; two handles 23 are disposed symmetrically and peripherally on the broad brim 21.

The third embodiment of the present invention is illustrated in FIGS. 5-8. The third embodiment differs from the first embodiment in that the length of the opening 4 is shorter, which is preferably two thirds of that of the main body, and the opening 4, with a central angle of 180 degrees, is disposed only in the main body 1. In order to dispose the opening 4 and simultaneously make the instrument firm and good-looking, the central line of the opening 4 and the central line of the unhollowed portion of the broad brim 21 are designed in the same plane. More specifically, three hollowed-out structures 22 are distributed at equal intervals on the broad brim 21 for the convenience of suturing the broad brim 21 with the skin. More specifically, wavy projections 24 are disposed at the circumference of the broad brim 21 to prevent the instrument from slipping down from the doctor's hand and to enable the broad brim 21 with certain friction. In order that the doctor can better observe the tissues during the surgical operation, the instrument of the present invention is double-colored injected, wherein the main body 1 and the broad brim 21 are made of transparent material, and the cone-shaped body 31 is in white or other colors.

The fourth embodiment of the present invention is illustrated in FIGS. 9-12. The fourth embodiment differs from the third embodiment in that the inserting guider 3 is made as a chamfer 32 on the front end 11 of the main body 1 in order to save material for producing the instrument of the present invention.

The fifth embodiment of the present invention is illustrated in FIGS. 13-16. The fifth embodiment differs from the third embodiment in that the suture junction 2 is made as holes 25 on the rear end 12 of the main body 1. When the instrument of the present invention is inserted to the operating position, the main body 1 is fixed with the patient's tissues by threading lines through the holes 25.

Figure 21:
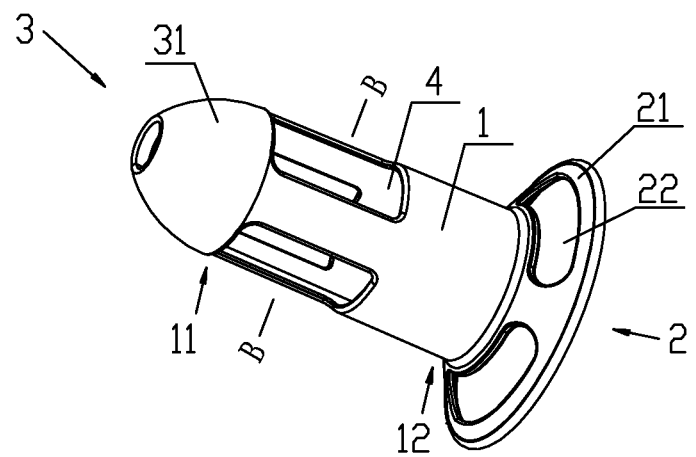
FIG. 21 is a schematic view of the instrument for anorectal surgery according to the seventh embodiment of the present invention.
Figure 22:
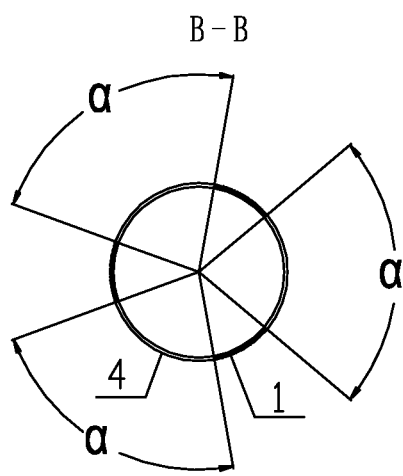
FIG. 22 is a sectional view cut along B-B line in FIG. 20.

The sixth embodiment of the present invention is illustrated in FIGS. 17-20. The sixth embodiment differs from the third embodiment in that two openings 4 are symmetrically made in the wall of the main body 1 and the central angle α of the opening 4 is from 30 degrees to 160 degrees, preferably 120 degrees. Two openings 4 are disposed in this embodiment in order to be convenient for the surgical operation of non-circular cutting for double hemorrhoids and in order that all or part of the mucosa and tissues at two operating positions can be pulled into the hollow interior of the main body through the two openings 4 to cut. Of course, technical solutions with asymmetrical openings or openings of different sizes according to the specific conditions of the hemorrhoids and tissues are also covered by the scope of the present invention. As shown in FIG. 21 and FIG. 22, in the seventh embodiment of the present invention, three openings 4 with different length are disposed in the wall of the main body 1, and the central angle of each opening is 80 degrees. In this embodiment, all or part of the mucosa and tissues can get into the interior of the main body 1 through the three openings 4. Of course, because all or part of the mucosa and tissues are not distributed evenly on the anal canal, the central angles of the three openings can be different. To meet the manufacturing requirements, two of the three openings may be designed to be the same and the other one different, e.g., the respective central angle for two openings is 90 degrees and that for the other opening is 75 degrees.

Figure 23:
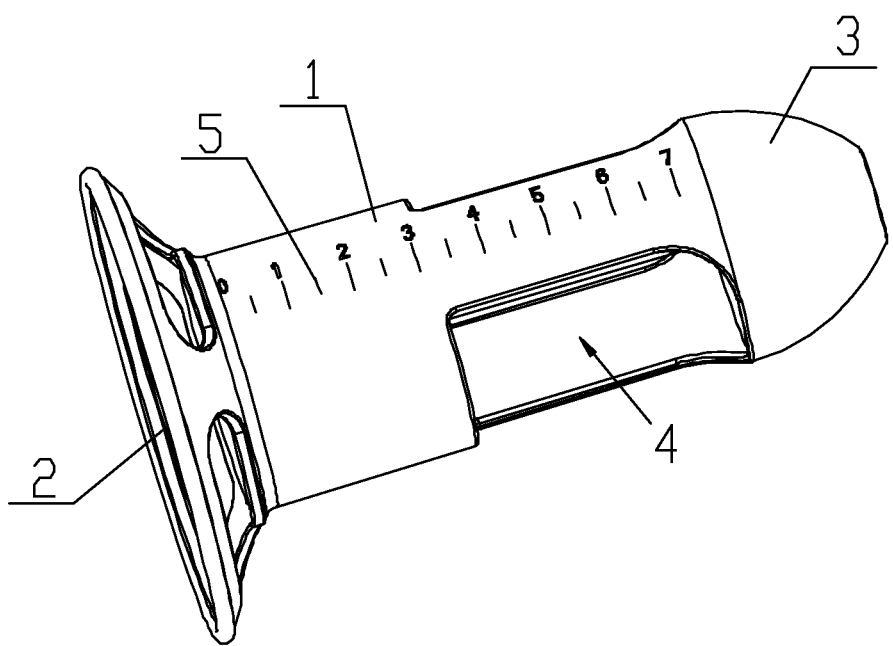
FIG. 23 is a schematic view illustrating the instrument for anorectal surgery according to the eighth embodiment of the present invention.
Figure 24:
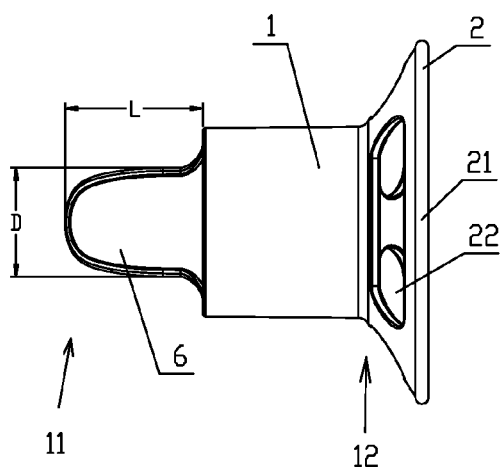
FIG. 24 is a front view of the instrument for anorectal surgery according to the ninth embodiment of the present invention.
Figure 25:
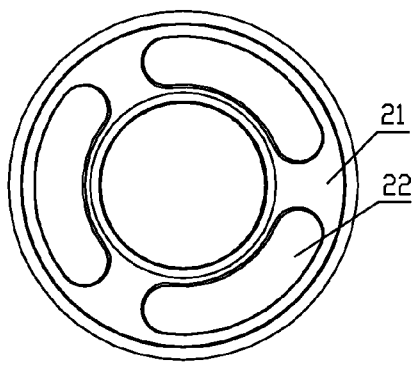
FIG. 25 is a right view of the ninth embodiment of the present invention.
Figure 26:
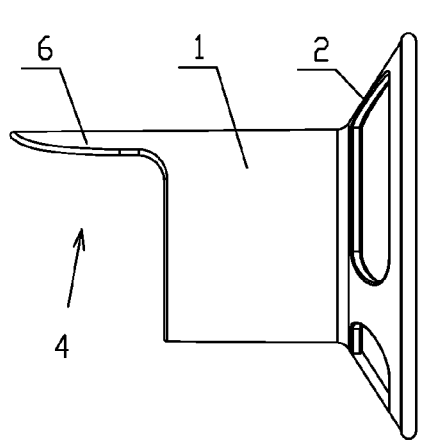
FIG. 26 is a top view of the ninth embodiment of the present invention.
Figure 27:
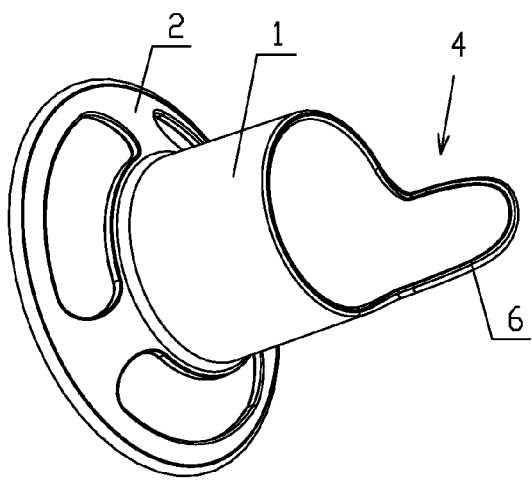
FIG. 27 is a stereo view of the ninth embodiment of the present invention; in which, the elements are denoted as follows.

What has to be mentioned is that, in all embodiments of the present invention, a scale 5 can be disposed in the wall of the main body 1 to display how deep the main body enters the anus. The scale 5 covers part or all of the main body 1, namely, the scale may be disposed around the main body in order that the doctor can see the scale from any visual angles, or the scale may be disposed in part of the main body and the doctor can see the scale from a certain visual angle by rotating the instrument, which is the case in the eighth embodiment as shown in FIG. 23, wherein the scale 5 is made directly on the main body 1 by injection. Thanks to the scale 5, the doctor knows how deep the main body 1 enters the anus and provides more clear instructions for the surgical operation. The scale 5 of the present invention can be made in other forms, such as mechanical, digital or graph-text indications, in addition to the numerical indications as illustrated in this embodiment.

The operating method of the instrument will be described in details with an example of the anorectal surgery of non-circular cutting for hemorrhoids. Firstly, put the inserting guider 3 of the instrument towards the anus and insert the instrument into the anal canal. Secondly, rotate the instrument to make the openings 4 direct at all or part of the mucous and tissues. Thirdly, suture the suture junction 2 of the instrument with the skin around the anus to fix the instrument. Now the instrument of the present invention is located at the operating position.

Then perform purse-string suture for the mucous and tissues at the openings of the instrument with a curved needle held by a clamp. Put a circular stapler, of which the anvil is far away from the staple casing, into the instrument. After all or part of the mucous and tissues come in the suture area of the instrument, pull and tighten the purse-string to ensure all or part of the mucous and tissues are collected in the suture area of the instrument. Adjust the circular stapler to make the anvil close to the staple casing until the mucous and tissues are clamped tightly by the anvil and the staple casing. Subsequently, trigger pins of the circular stapler by a trigger handle to suture the tissues, while cut all or part of the mucous and tissues, and finally, withdraw the instrument.

It is apparent from the above description with reference to the accompanying drawings that, distinguished from a surgical operation with the conventional anal cannula, during the surgical operation with the instrument of the present invention, it is not necessary to use a cannula and an anoscope, and the corresponding processes for operating the two instruments are omitted, which makes the whole operation simpler and reduces the operation time. Furthermore, with the aid of the present invention, the circular stapler can be applied to the anorectal surgery of non-circular cutting for hemorrhoids, which extends the application scope of the circular stapler and further ensures the effect of the operation, and it is worth to promote the present invention in this field.

The ninth embodiment of the present invention is illustrated in FIGS. 17-20, which is an optimal design of the fourth embodiment. On the front end 11 of the main body 1 are disposed a curved wall 6 and an opening 4 opposite to the curved wall 6, the tissues need to be cut can get into the hollow interior of the main body 1 through the opening 4. In this embodiment, the length of the main body is from 20 mm to 50 mm, preferably 40 mm. The length L of the curved wall 6 is from 10 mm to 70 mm, and the width D is also from 10 mm to 70 mm. The ranges are preferred according to human's anal tissues. Now there are seven optimal combinations of the length and the width of the curved wall 6: L*D is 30*30, 30*25, 30*20, 25*30, 25*25, 40*25 and 50*25 respectively. Furthermore, in this embodiment, the foremost-end of the curved wall 6 is curved, equivalent to a chamfer, which guides the instrument to the operating position without scratching other tissues.

The operating method of the ninth embodiment will be described in details with an example of the anorectal surgery of rectocele. Firstly, insert the instrument into the anus, and rotate the instrument to make the curved wall 6 opposite to the mucous and tissues of the rectocele, namely, to block the normal tissues from falling into the hollow interior of the main body 1 by the curved wall 6. Secondly, perform purse-string suture for the tissues of the rectocele with a curved needle; afterwards, put the circular stapler at the operating site and pull the mucous and tissues sutured into the cavity of the circular stapler through the opening 4; then cut and suture the mucous and tissues of the rectocele with the circular stapler, finally now the mucous and tissues of the rectocele are cut and the wound is closed tightly. The operation is simple, fast and effective.

It should be understood that the present invention may be implemented in other embodiments than those described above. Any equivalent substitutions or variations can be made without departing from the spirit and scope of the invention as defined in the claims. For example, the handles in the first and the second embodiments can be applied to other embodiments. Similarly, the wavy projections in the third embodiment can applied to the first and the second embodiments. Moreover, the main body 1 of the present invention can be made into other streamlined shapes, in addition to the cylindrical and the conical shapes described in the embodiments. The chamfer in the fourth embodiment can be omitted, and the main body can be inserted into the patient's body directly. The number of the openings is not limited to one or two that is described in the embodiments but can be more.

What is claimed is:

1. An instrument for anorectal surgery, comprising
a hollow main body, the main body includes a front end and a rear end, the rear end of the main body has a closed-ring cut section; the main body is configured for reaching an operating position through an anus;
a suture junction integrated with the rear end of the main body and extending from the rear end of the main body; and
an inserter guider integrated with the front end of the main body, and extending forward from the front end of the main body for guiding the instrument for anorectal surgery to the operating position;
whereby the main body is pushable to an operating position by operating the suture junction and is fixable by suturing the suture junction on tissues;
wherein the suture junction comprises a broad brim having a diameter greater than that of the main body, and the broad brim is backwardly divergent in shape,
wherein two or three openings, which are always open during insertion, rotation and removal, are provided in a front wall of the closed-ring cut section of the main body, enabling tissues, which need to be cut, into a hollow interior of the main body through one of the openings;
wherein the inserter guider comprises a cone-shaped body with a closed wall; and
wherein the suture junction and the inserter guide are integrated with the main body.

2. The instrument according to claim 1, wherein the broad brim has at least two hollowed-out structures which are disposed evenly on the broad brim.

3. The instrument according to claim 1, wherein wavy projections are disposed at a circumference of the broad brim.

4. The instrument according to claim 1, wherein the main body is cylindrical or conical.

5. The instrument according to claim 1, wherein two openings are made in a wall of the main body and each opening has a central angle ($\alpha$) ranging from 30 degrees to 160 degrees.

6. The instrument according to claim 5, wherein the two openings are made symmetrically in the wall of the main body and the central angle ($\alpha$) of each opening is 120 degrees.

7. The instrument according to claim 1, wherein three openings are made evenly in a wall of the main body; and central angles of the three openings are all equal, or all different, or two of the central angles are equal.

8. The instrument according to claim 1, wherein a length of the opening is in the range of one sixth to five sixths of length of the main body.

\* \* \* \* \*